US008337916B2

(12) United States Patent
Gokaraju et al.

(10) Patent No.: US 8,337,916 B2
(45) Date of Patent: Dec. 25, 2012

(54) **USE OF *APHANAMIXIS POLYSTACHA* EXTRACTS OR FRACTIONS AGAINST 5-LIPOXYGENASE MEDIATED DISEASES**

(75) Inventors: Ganga Raju Gokaraju, Vijayawada (IN); Rama Raju Gokaraju, Vijayawada (IN); Trimurtulu Golakoti, Vijayawada (IN); Venakteswara Rao Chirravuri, Vijayawada (IN); Venkata Krishna Raju Alluri, Vijayawada (IN); Kiran Bhupathiraju, Vijayawada (IN)

(73) Assignee: Laila Nutraceuticals, Vijayawada (IN)

( * ) Notice: Subject to any disclaimer, the term of this patent is extended or adjusted under 35 U.S.C. 154(b) by 246 days.

(21) Appl. No.: 12/602,573

(22) PCT Filed: Jun. 1, 2007

(86) PCT No.: PCT/IN2007/000221
§ 371 (c)(1),
(2), (4) Date: Dec. 1, 2009

(87) PCT Pub. No.: WO2008/146298
PCT Pub. Date: Dec. 4, 2008

(65) Prior Publication Data
US 2010/0178288 A1   Jul. 15, 2010

(51) Int. Cl.
*A61K 36/00* (2006.01)
(52) U.S. Cl. .................................. 424/775; 424/725
(58) Field of Classification Search .................. None
See application file for complete search history.

(56) References Cited

U.S. PATENT DOCUMENTS

| | | | |
|---|---|---|---|
| 4,473,551 | A | 9/1984 | Schinitsky |
| 4,687,781 | A | 8/1987 | Ehrenpreis et al. |
| 4,777,174 | A | 10/1988 | Sunshine et al. |
| 6,346,278 | B1 | 2/2002 | Macrides et al. |
| 6,521,268 | B2 | 2/2003 | You et al. |
| 6,537,977 | B1 | 3/2003 | Kyogashima et al. |
| 2006/0167097 | A1* | 7/2006 | Ramachandran et al. .... 514/559 |
| 2006/0172012 | A1* | 8/2006 | Finley et al. .................. 424/523 |

FOREIGN PATENT DOCUMENTS

| | | |
|---|---|---|
| KR | 4103984 A | 12/2004 |
| WO | 8809654 A1 | 12/1988 |
| WO | 03047599 A1 | 6/2003 |

OTHER PUBLICATIONS

Harmon et al. The Structure of Rohitukine, the main alkaloid of *Amoora rohituka* (Syn. *Aphanamixis polystachya*), Tetrhedron Letters No. 8, pp. 721-724, Pergamon Press Ltd. 1979. Printed in Great Britain.*
The Wealth of India, A Dictionary of Indian Raw Material & Industrial Products, Raw Materials vol. 1:A, pp. 318-320.*
Sarkar et al. "Pharmacognostic Evaluation of *Aphanamixis polystachya* Seed Drug", Homoeopathic Pharmacopoeia Laboratory, Ghaziabad-201002.*

Erik Lubberts, "IL-17/Th17 targeting: On the road to prevent chronic destructive arthritis?", Cytokine, vol. 41 (2008), pp. 84-91.*
Bora et al. "Anti-inflammatory effects of specific cyclooxygenase 2,5-lipoxygenase, and inducible nitric oxide synthase inhibitors on experimental autoimmune anterior uveitis (EAAU)" Ocul Immunol Inflamm. Apr.-Jun. 2005;13(2-3):183-9.*
T. Rabi "Antitumour activity of amooranin from *Amoora rohituka* stem bark" (Current Science, vol. 70, No. 1, Jan. 10, 1996).*
Sarkar M et al., Pharmacognostic Evaluation of *Aphanamixispolystachya* Seed Drug, Journal of Economic and Taxonomic Botany, Scientific Publishers, Jodhpur, IN. vol. 15, No. 1, 1991, pp. 121-127.
Bhuyan M A K et al., Antimicrobial activity of oil and crude alkaloids from seeds of *Aphanamixis polystachya* (Wall.) R. N. Parker, Bangladesh Journal of Botany, Bangladesh Botanical Society, Dacca, BD, vol. 29, No. 1, Jun. 2000.
Lakdawala A D et al., Immunopharmacological potential of rohitukine: a novel compound isolated from the plant *Disopylum binectariferum*, Asia Pacific Journal of Pharmacology, Singapore University Press, SG, vol. 3, No. 2, 1988, pp. 91-98.
Harmon, AD et al., The structure of rohitukine, the main alkaloid of *Amoora rohituka* (syn. *Aphanamixis polystachya, Meliaceae*) Tetrahedron Letters, vol. 8, 1979, pp. 721-724.
Robinson et al., Inflammatory disease of CNS II: Meningitis and cerebral abscess, ACNR vol. 4 No. 4 Sep./Oct. 2004.
Fraenkel et al., Informed choice and the widespread use of anti-inflammatory drugs, Arthritis & Rheumatism, vol. 51, No. 2, Apr. 14, 2004, pp. 210-214.
Chanda, the Wealth of India Raw materials, 1985, vol. I (A) pp. 318-320.
Rabi et al., Antitumor and cyctotoxic investigation of *Amoora rohituka*, International Journal of Pharmacognosy, V. 33 (4): pp. 359-361, 1995.
Rabi, Antitumor activity of amooranina from *Amoora rohituka* stem bark. Current Science, V. 70(1): pp. 80-81, 1996.
Gole et al., Hepatoprotective effect of *Amoora rohituka*, International Journal of Pharmacognosy, V. 35(5):pp. 318-322, 1997.
Kundu et al., Aphananin a triterpene from *Aphanamixis polystacha*. Phytochemistry. V. 24, 2123-2125, 1985. Chandrasekharan et al., Aphanamixol a diterpene alcohol from *Aphanamixis polystacha* (wall) Parker, J. Indian Chem. Soc., 45, 208, 1968.
Sengupta et al., Triglyceride composition of *Amoora rohituka* seed oil. Amm. Oil. Chem. Soc., V. 53, 478-7, 1976.
Sodhala; Gadanigrahah ed, Ganga Sahaya Pandeya & Com. Indradeva Tripathi, Part I (Prayoga Khanda) Chaukhamba Sanskrit Sansthan, Varanasi, Ed. 3rd 1999 pp. 214-215.
Bhavamisra; Bhavaprakasa—Edited & translated by Brahmasankara Misra, Part-II: Chaukhamba Sanskrit Sansthan, Varanasi, Edn 7th 2000 p. 820.
Govinda Dasa; Bhaisajya Ratnavali—Edited by Rajeshvaradutta Shastri, Translated by Ambikaduttashastri: Chaukhamba Sanskirt Sansthan, Varanasi, Edn. 14th 2001 p. 550.

* cited by examiner

*Primary Examiner* — Christopher R. Tate
*Assistant Examiner* — Deborah A. Davis
(74) *Attorney, Agent, or Firm* — Kramer & Amado, P.C.

(57) ABSTRACT

The invention discloses 5-lipoxygenase inhibitory product prepared from botanical sources. More specifically, the invention describes 5-lipoxygenase inhibitory extracts or bio-enriched extracts or fractions of *Aphanamixis polystachya*, methods of making 5-lipoxygenase inhibitory extract, and methods of treating and/or preventing disease conditions mediated by 5-lipoxygenase by using the said extract. The invention further discloses pharmaceutical or nutraceitical or dietary compositions containing therapeutically effective amounts of the extracts of *Aphanamixis polystachya* in combination with other known anti-inflammatory agents useful for oral, parenteral and topical administration.

6 Claims, 2 Drawing Sheets

USE OF *APHANAMIXIS POLYSTACHA* EXTRACTS OR FRACTIONS AGAINST 5-LIPOXYGENASE MEDIATED DISEASES

FIELD OF THE INVENTION

The invention relates generally to 5-lipoxygenase inhibitory products and, more specifically, to 5-lipoxygenase inhibitory extracts or fractions derived from *Aphanamixis polystachya*. More particularly, the present invention relates to bio-enhancement of extracts and a process for the preparation of the same from *Aphanamixis polystachya*.

The present invention further relates to 5-lipoxygenase inhibitory extracts for treating disease indications mediated by 5-lipoxygenase enzyme, methods of making an 5-lipoxygenase inhibitory composition, and methods of treating and/or preventing arthritis, asthma, ulcerative colitis and similar responses.

BACKGROUND OF THE INVENTION

Inflammatory diseases affect more than fifty million Americans. As a result of basic research in molecular and cellular immunology over the last ten to fifteen years, approaches to diagnosing, treating and preventing these immunity-based diseases has been dramatically altered. Inflammation is a complex protective biological process triggered by irritation, injury or infection, characterized by redness, heat (due to increased blood flow), swelling (due to increased vascular permeability), loss of function and pain (due to sensitization of pain receptors). In addition to the foregoing induced conditions, inflammation can also occur due to age related factors. Additionally, inflammatory response can be undesirably triggered in response to noninfectious agents in individuals having allergies and/or autoimmune diseases. Chronic inflammatory condition and cancer have become emerging health concern in a number of countries across the globe. Inflammation has proven to be part of etiology of several chronic diseases like vasculitis, atherosclerosis, ulcerative colitis, inflammatory bowel syndrome, diabetes, Alzheimer's, Meningitis etc., (Susan Robinson & William Stewart, Inflammatory disease of CNS II: Meningitis and cerebral abscess, ACNR VOLUME 4 NUMBER 4 SEPTEMBER/OCTOBER 2004). Non-steroidal anti-inflammatory drugs are most commonly used remedies for inflammatory diseases. Phytochemicals from certain plants were reported to demonstrate anti-inflammatory properties. Like aspirin many -NSAIDS are presumed to work by blocking cyclooxygenase, lipoxygenase and phospholipase. Presently, there has been a tremendous surge in demand for natural non-steroidal anti-inflammatory drugs (NSAIDs) because of their established safety and efficacy, through decades of usage by various cultures (Liana Fraenkel, Dick R. Wittink, John Concato and Terri Fried, Informed choice and the widespread use of anti-inflammatory drugs, Arthritis & Rheumatism, Vol. 51, No. 2, Apr. 15, 2004, pp 210-214). The inflammatory and carcinogenesis processes are known to be triggered by increased metabolic activity of arachidonic acid.

The Arachidonic acid pathway constitutes one of the main cellular mechanism for mediating inflammation. Arachidonic acid diverges down into two main pathways during this process, one is the cyclooxygenase (COX) pathway and the other is lipoxygenase (LOX) pathway. The COX pathway leads to prostaglandins and thromboxane production, where as the LOX pathway leads to leukotrienes (LTS) and hydroxyl eicosatetetraenoic acid (HETEs). These classes of inflammatory molecules exert profound biological effects, which enhance the development and progression of human cancers such as colon, breast, lung, prostrate and pancreas.

Leukotrienes and 5(S)-HETE are important mediators for inflammatory, allergic and obstructive process. Leukotrienes increase microvascular permeability and are potent chemotactic agents. Inhibition of 5-lipoxygenase indirectly reduces the expression of TNF-α(a cytokine that plays a key role in inflammation). 5-Lipoxygenase is therefore the target enzyme for identifying inhibitors, which have potential to cope with a variety of inflammations and hypersensitivity-based human diseases including asthma, arthritis, bowel diseases such as ulcerative colitis and circulatory disorders such as shock and ischemia.

Similarly prostaglandins are intercellular messengers that are produced in high concentration at the sites of inflammation and are capable of causing vasodilatation, increased vascular permeability and sensitizing pain receptors. The proinflammatory prostaglandins (PGE2) are produced by inducible isoform cyclooxygenase-2 (COX-2). The prostaglandins that are important in gastrointestinal and renal function are produced by the constitutively expressed isoform, cyclooxygenase-1 (COX-1). COX-1 is the protective housekeeper isoform and it regulates mucosal cell production of mucous membrane that provides a barrier between the acid and pepsin present in gastric secretions. Non-selective COX inhibitors thus produce serious GI side effects. Scientists around the world are thus investing major efforts in identifying non-steroidal anti-inflammatory drugs that inhibit 5-lipoxygenase and cyclooxygenase-2 enzymes. However COX-2 inhibitors are known to have adverse effects on cardiovascular system. A selective COX-2 inhibitor Vioxx (rofecoxib) was withdrawn from the U.S. and worldwide markets on Sep. 30, 2004 due to safety concerns of an increased risk of cardiovascular events.

Various anti-inflammatory substances have heretofore been used, for example, such as steroids like cortisone, dexamethasone; nonsteroids like anthranilic acid derivatives, salicylates, indomethacin, benzydamine and enzymes like proteases. Because of considerable side effects, however, it has been difficult to use these conventional substances in doses sufficient to produce satisfactory anti-inflammatory activities.

*Aphanamixis polystachya* Wall & Parker also known as *Amoora rohituka* (Roxb); Wight & Arn Family: maliaceae, is an evergreen medium sized tree with a dense spreading crown and a straight cylindrical trunk that grow up to 15 m in height and 1.5 to 1.8 m in girth. It is widely distributed in sub Himalayan tract from Gonda (UP) eastwards to Bengal, Sikkim and Assam; west wards to Western ghats and Andaman (Y. R. Chanda, The Wealth of India Raw materials, 1985, Vol-I (A) pp 318-320). Various parts of the plant are used in Indian traditional medicine because of their hepatoprotective, antibacterial, anthelmintic and antirheumatic properties. The bark is acrid, depurative and acts as urinary astringent. (Y. R. Chanda; "The Wealth of India Raw materials", 1985, Vol-I (A) pp 318-320).

Ayurveda prescribes *rohituka* exclusively for disorders related to spleen and liver. The ethanolic extract of the stem bark of *A. polystachya* showed anti-tumor activity, and its metabolites, amooranin and prieurianin were identified as active principle responsible for its anti-tumor activity. Amooranin, the triterpene acid reduced the tumor size of mammary adenocarcinoma in animals induced with o-nitrosomethyl urea. The stem bark prolonged the mean survival time of Daltons lymphoma tumor baring mice. (Rabi T., Gupta R. C., Antitumor and cytotoxic investigation of *Amoora rohituka*, International Journal of Pharmacognosy, V. 33(4): pp. 359-

361, 1995 & Rabi T., Antitumor activity of amooranin from *Amoora rohituka* stem bark. Current Science, V. 70(1): pp. 80-81, 1996). The bark also possesses mild relaxant, cardiotonic, hepatoprotective and cholerectic activities and exhibits analgesic, immunosuppressive and antidiabetic properties (Gole M. K., Dasgupta S., Sur R. K. and Ghosal J., Hepatoprotective effect of *Amoora rohituka*, International Journal of Pharmacognosy, V. 35(5): pp. 318-322, 1997).

Phytochemical investigations of the plant *A. rohituka* have resulted in the isolation and identification of several triterpenoids (Kundu, A. B., Ray, S., Chrtteijee, A., Phytochemistry. V. 24, 2123-45, 1985; Rabi, T., Curr. Sci., V 70, p 80, 1996; Chandrasekhar, S., Chakaraborthy, T., J. Indian. Chem. Soc., 208, 1968; The stem bark also contained myristicin eugenol and phenolic compounds and seed oil contained triglyceride composition (Sengupta A Mazumder, U. K., J. Amm. Oil. Chem. Soc., V. 53, 478-7, 1976).

The roots are reputed in the indigenous system of medicine as a cure for diarrhea and dysentery. The stem extract of *Aphanamixis polystachya* shows hepatoprotective activities. The bark, fruit and leaves of *Aphanamixis polystachya* taste bitter and are widely used in folk medicine. The bark is commonly used as astringent and used in the treatment of diseases of the liver and spleen for tumors and abdominal complaints. The powdered bark is also used in the treatment of rheumatism. Various parts of the plant are used in Bengali traditional medicine because of their anticancer, antimicrobial, antiinflammatory and hepatoprotective properties.

However, despite of its pharmacological and nutritional benefits, the 5-lipoxygenase inhibitory benefits of *A. polystachya* is not known. Therefore, there remains a need in the nutraceutical art for nutraceutical composition that offers the health benefit of *A. polystachya* plant. Further there is a need for natural extract of the said plant for treating inflammatory diseases.

There is an ample literature pertaining to anti-inflammatory activity of plant extracts are available in the prior art.

U.S. Pat. No. 6,521,268 describes antibacterial and anti-inflammatory compositions with *Inula helenium* L. extract and water soluble chitosan.

U.S. Pat. No. 6,537,977 describes anti-inflammatory agent and a pharmaceutical composition, which contains glycosaminoglycan having at least one sulfate group or a pharmaceutically acceptable salt along with an immunosuppressant.

U.S. Pat. No. 4,777,174 describe novel analgesic and anti-inflammatory compositions comprising caffeine together with a selected non-narcotic analgesic or non steroidal anti-inflammatory drug or a selected narcotic analgesic, or both.

U.S. Pat. No. 4,473,551 describes a composition and method for the treatment of disorders having an inflammatory component comprising essentially whole cartilage, or a greater than 100,000 molecular weight fraction obtained from an aqueous extract, in combination with glucosamine or a substance affording glucosamine under the conditions of treatment, administered topically or parentally.

U.S. Pat. No. 6,346,278 describes anti-inflammatory, and particularly anti-arthritic, treatment of a human or animal patient comprising administration of an effective amount of a lipid extract of Perna canaliculus or Mytilus edulis to the said subject.

U.S. Pat. No. 4,687,781 describes analgesic and anti-inflammatory compositions, which comprises a therapeutically effective amount of hydrocinnamic acid alone, or in combination with one or more amino acids selected from the group consisting of D-phenylalanine, DL-phenylalanine, D-leucine, and DL-leucine and synergistically effective amount of a second therapeutic agent selected from the group consisting of aspirin or an aspirin-type non-steroidal anti-inflammatory and anti-pyretic agent.

WO03047599A1 provides an anti-inflammatory composition containing iridoid glycoside compound, catalposide isolated from stem bark of Catalpa ovata as an active ingredient for treating inflammatory response by inhibiting inducible nitric oxide synthase iNOS, NF-κB, TNF-alpha, IL-1beta and IL-6.

WO8809654A1 describes depigmentation and anti-inflammatory compositions containing mulberry extract and optionally hydroquinone and kojic acid.

KR4103984A describes anti-inflammatory composition containing the extracts of bojungikgitang or kagam-bojungikgitang as active ingredient which has no adverse side effect on human body. The anti-inflammatory composition is characterized by containing the extract of bojungikgitang which is composed of ginseng, *Astragalus membranaceus* (FISCH.) BGE, *Angelica gigas* Nakai, Atractylodes Rhizoma Alba, *Citrus Aurantium* L. subsp, *Nobilis* markino, licorice root, *Bupleurum falcatum* L., and *Cimicifyga simplex* Worm, or kagam-bojungikgitang which is composed of ginseng, *Astragalus membranaceus* (FISCH.) BGE, *Angelica gigas* Nakai, Atractylodes Rhizoma Alba, *Citrus Aurantium* L. subsp, *Nobilis markino*, licorice root, Artemisiae iwayomogii Herba and Scutellariae Radix.

Thus none of the prior art mentioned above describes the use of powder or extract derived from *Aphanamixis polystachya* and its applications, as a 5-lipoxygenase inhibiting agent and there has been no attempt to treat 5-lipoygenase mediated disorders using *Aphanamixis polystachya* extract.

There exists a need for nutraceutical composition that offers the health benefits of *Aphanamixis polystachya*. There also exists a need for pharmaceutical composition containing *Aphanamixis polystachya*. Further there is a need for natural product containing the said extract with other anti inflammatory agents, which inhibit 5-lipoxygenase enzyme.

Therefore the present invention is directed to a novel use of extract or fraction derived from *Aphanamixis polystachya* to treat 5-lipoxygenase mediated disorders in animals or humans.

It is therefore an object of the present invention to provide a non-toxic dietary supplement composition, which inhibits 5-lipoxygenase enzyme and prevents or cure 5-lipoxygenase mediated disorders, like, but not limited to rheumatoid arthritis, periodontal disease, asthma, bowel disease such as ulcerative colitis, circulatory disorders such as shock and ischemia, free radical mediated disorders such as Alzheimer's, Parkinson's and cardiovascular disease.

Thus the invention is directed to a novel mechanism of action of *A polystachya* plant extract or fraction, which exhibit 5-lipoxygenase inhibitory activity and a process of extracting or fractionation thereof.

SUMMARY OF THE INVENTION

In accordance with the above object, the invention provides 5-lipoxygenase inhibitory extract or fractions or compositions derived from *Aphanamixis polystachya* plant useful for treating and preventing 5-lipoxygenase mediated responses.

In one aspect, the present invention provides nutraceutical compositions derived from the *Aphanamixis polystachya* plant; particularly, provides efficacious nutraceutical compositions.

Accordingly, a main object of the present invention is the provision of novel 5-lipoxygenase inhibitory active agents from *Aphanamixis polystachya*.

Accordingly, in another aspect, the invention provides a substance capable of producing excellent 5-lipoxygenase inhibitory activities, which is substantially free of side effects. In a further aspect, the invention provides an anti-inflammatory substance capable of giving potent 5-lipoxygenase inhibitory activity at a smaller dose and free of side effects.

Another aspect of this invention provides excellent 5-lipoxygenase inhibitory compositions containing a mixture of *Aphanamixis polystachya* extract or fraction and one or more of other known anti-inflammatory agents as an effective therapeutic combination.

A further aspect of the present invention provides an extract or fractions of *Aphanamixis polystachya*, with a very effective combination of both 5-lipoxygenase inhibitory activity and antioxidant activity.

Still another aspect provides a process for producing 5-lipoxygenase inhibitory substance from *Aphanamixis polystachya*, said 5-lipoxygenase inhibitory substance exhibiting high efficacy against 5-lipoxygenase mediated diseases free from any harmful effects.

The provision of novel nutraceutical composition that contributes to general human wellness and good health has become another aspect.

The provision of nutraceutical composition that offers the holistic benefits of the *Aphanamixis polystachya* plant has become one more aspect of the invention. An additional aspect of the invention is to provide an antimicrobial and anti-inflammatory, antioxidant composition containing a therapeutically effective amount of extract or powder derived from *Aphanamixis polystachya*.

An additional aspect of the invention is to provide a process for preparing nutraceutical compositions of the *Aphanamixis polystachya* plant yielding the holistic benefits.

Yet another aspect of the present invention is to provide an economical process for manufacturing nutraceutical compositions of the *Aphanamixis polystachya* plant.

A novel use of extract derived from *Aphanamixis polystachya* which exhibits antioxidant, 5-lipoxygenase inhibition, and anti-arthritic properties devoid of adverse effects has become another aspect of the invention.

It is also an aspect of the invention to provide a non asthma aggravating 5-lipoxygenase inhibitor, which can further reduces leukotriene biosynthesis and ameliorate air way inflammation during bronchial asthma.

Still another aspect of the present invention is to identify the mechanism of activity by in vitro assays.

The invention further describes a process for preparation of enriched extract or powder derived from *Aphanamixis polystachya*.

Yet, in a further aspect, the invention provides methods for treating and/or preventing a condition involving over production of 5-lipoxygenase or inflammatory markers response comprising administering a therapeutically effective amount of a composition comprising a 5-lipoxygenase inhibitory product of *Aphanamixis polystachya* plant to an individual.

Other aspects of the present invention will become evident upon reference to the attached figures and following detailed description.

DETAILED DESCRIPTION OF THE INVENTION

While the invention will now be described in detail in connection with certain preferred and optional embodiments, so that various aspects thereof may be more fully understood and appreciated.

In accordance with the above aspects, the invention describes a novel 5-lipoxygenase inhibitory extracts or fractions or compositions derived from *Aphanamixis polystachya* plant useful for treating and preventing 5-lipoxygenase mediated responses. The invention demonstrates that the enriched extract product of *Aphanamixis polystachya* possess significant 5-lipooxygenase inhibitory activity. The *Aphanamixis polystachya* thus modulate all the disease conditions mediated by 5-lipoxygenase. The invention comprises extracts derived from natural sources that effectively suppress, inhibit, disease conditions in individuals, which are mediated by 5-lipoxygenase enzyme. Therefore, the *Aphanamixis polystachya* extract can be administered to any individual to treat or prevent a condition involving a 5-lipoxygenase response. Additionally, the 5-lipoxygenase inhibitory extract may be formulated as pharmaceutical compositions (e.g., an ethical drug), nutraceutical compositions (e.g., a dietary supplement), cosmeceuticals (e.g., a cosmetic product having biologically active ingredients), or as a food or beverage additive.

The present invention provides powder or extract and methods for reducing 5-lipoxygenase mediated diseases. In particular, the invention provides powder or extract isolated or derived from *Aphanamixis polystachya* plant for use in treating osteoarthritis in patients prophylactically and/or therapeutically.

As used herein, the term "extract product" refers to any compound, any agent and/or mixtures thereof that are obtained, isolated, and/or derived from an extract of the plant material. The term "plant material" refers to any plant material including, but not limited to, leaves, stems, flowers, fruits, seeds, roots, bark and combinations thereof.

As previously described, the 5-lipoxygenase inhibitory composition is isolated by extracting plant material of an *Aphanamixis polystachya* plant. The plant material may be selected from a group consisting of leaves, stem, flowers, fruits, roots, bark and combinations thereof.

The present invention describes a process for preparation of extract from *Aphanamixis polystachya*, the said process comprises of extracting dried and powdered bark of *Aphanamixis polystachya* with polar solvent selected from a group consisting of water or alcohol and any mixtures thereof with or without prior extraction with ethyl acetate (EtOAc).

In a preferred embodiment of the invention, *A. polystachya* bark is dried under shade temperature ranging between 25 to 30° C. Dried bark of plant, *A. polystachya* is ground to coarse powder. The powder thus obtained is extracted with hydroalcohol at a temperature range of 60 to 65° C. for 2 to 3 hrs. Extraction process is repeated thrice using hydroalcohol in the ratio 1:10-1:15 W/V with respect to the plant material. The combined extracts are fine filtered. The filtrate is evaporated to dryness under reduced pressure at 40 to 50° C. on a climbing film evaporator. The crude hydroalcoholic extract is then subjected to solvent partitioning between water and ethyl acetate. The organic layer is separated and the aqueous layer is evaporated under reduced pressure to obtain dry powder. The dry powder is dissolved in water and loaded on to a R20 (Styrene-divinylbenzene Synthetic Adsorbent resin, Mitsubishi Chemical Corporation, Japan) resin column. The column is washed with two bed volumes of water. The compound is then eluted with 60% methanol, and 80% methanol, followed by washing with methanol. The fractions eluted with 60%-80% methanol are combined and concentrated to yield the active fraction as a dry powder.

In another preferred embodiment, the active fraction/extract thus obtained from the above process can be used in pharmaceutical preparation. The form of pharmaceutical preparation can be selected in accordance with the purpose of use. The form of preparation thus can be selected from the group consisting of solids, such as tablets, granules, powders, pills, capsules, etc., and liquids such as suspensions, emulsions, syrups, elixirs etc.

In another preferred embodiment, the invention provides methods of treating the patient with a therapeutically effective amount of *Aphanamixis polystachya* extract or fraction for controlling 5-lipoxygenase mediated diseases.

In another preferred embodiment, the extract or fraction can be used in pharmaceutical preparation, dietary supplements, nutritional supplements or nutraceutical preparations.

Moreover, food products ranging from ordinary food products to specialty health food products (functional food products) can be prepared using the above-mentioned extract or fraction of the present invention as the effective component. Moreover, said extract or fraction can be used as an additive for various food products. The types of food products are not limited to specialty health food products. The present invention can also be used in, but not limited to beverages.

The methods and compositions of the invention may also be useful in the treatment of allergic diseases, reactions, and conditions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies), such as asthma (particularly allergic asthma) or other respiratory problems.

The extract or fraction (and thus the methods) of the invention can be used alone or in conjunction with other therapies including, for example, administration of other therapeutic agents (including other anti-inflammatory compositions or formulations).

It will be appreciated that the treatment methods of the invention are useful in the fields of human medicine and veterinary medicine. Thus, the subject or individual to be treated may be a mammal, preferably human, or other animals. For veterinary purposes, subjects include, for example, farm animals such as cows, sheep, pigs, horses, and goats; companion animals such as dogs and cats; exotic and/or zoo animals; laboratory animals including mice, rats, rabbits, guinea pigs, and hamsters; and poultry such as chickens.

As previously indicated, the 5-lipoxygenase inhibitory extract may be formulated as pharmaceutical compositions, nutraceutical composition, and composition for topical administration.

5-lipoxygenase inhibitory extract product can be formulated as gels, ointments, lotions, creams, sprays, drops, suppositories, sprays, transdermal patches, or can be formulated for oral administration.

In another embodiment, 5-lipoxygenase inhibitory extract product derived from *Aphanamixis polystachya* can be used as a single ingredient or in combination with known anti-inflammatory agents. The 5-lipoxygenase inhibitory extract derived from *Aphanamixis polystachya* can be used in single or in combination with known anti-inflammatory agents, wherein anti-inflammatory agents include, but not limited to 3-O-acetyl-11-keto-β-boswellic acid, curcumins or demethylatedcurcumins, glucosamine, resveratrol, garlic extract, ginger extract, chondroitin, methylsulfonylmethane, bromelain, serratio peptidase, quercitine etc. The herbal composition can be administered orally, topically or parenterally. In addition to reducing the inflammation, the herbal composition also promotes healthy joint function due to its inhibitory action against 5-Liopxigenase (5-LOX) and other inflammatory biomarkers.

According to the invention, the 5-lipoxygenase inhibitory extract may be administered by any known route of administration to the subject/individual. For example, a composition comprising an 5-lipoxygenase inhibitory extract of an *Aphanamixis polystachya* plant can be formulated for injection or for oral, nasal, trans-dermal or other forms of administration.

ADVANTAGES OF THE PRESENT INVENTION

A novel use of extract or fraction derived from *Aphanamixis polystachya*, which exhibits antioxidant, 5-lipoxygenase inhibitory and anti-arthritic properties devoid of adverse side effects. The present invention provides a process for preparation of bio-enriched extract or fraction from *Aphanamixis polystachya*.

The following examples, which include preferred embodiments, will serve to illustrate the practice of this invention, it being understood that the particulars shown are by way of example and for purpose of illustrative discussion of preferred embodiments of the invention.

It will be appreciated by any person skilled in this art that the present invention includes the following examples and further can be modified and altered within the technical concept of the present invention.

EXAMPLES

Example 1

Method of Preparation of Hydroalcohol Extract of *Aphanamixis polystachya*

The 5-lipoxygenase inhibitory product was prepared using the following method. Dried bark of the plant material *A. polystachya* (1 Kg) was pulverized to coarse powder, extracted with hydroalcohol (6 L, methanol/water 6:4) at 90° C. for 1 h. Extraction process was repeated thrice using same solvent (6 L+4.5 L+4.5 L). All the extracts were combined and fine filtered, and the clear extract was evaporated to dryness on a climbing film evaporator at 50-60° C. to obtain a residue (190 g).

Example 2

Method of Preparation of Water Extract of *Aphanamixis polystachya*

The 5-lipoxygenase inhibitory product was prepared in the following method. Shade dried bark (1 Kg) of *A. polystachya* was pulverized to coarse powder, extracted three times with water (5 L+3 L+3 L) for 2 h at 70° C. The combined extracts were fine filtered and concentrated to dryness under reduced pressure to give a dry powder (125 g).

Example 3

Method of Preparation of Alcohol Extract of *Aphanamixis polystachya*

*Aphanamixis polystachya* bark powder (1 Kg) was extracted four times successively with methanol (5 L+3 L+3 L+3 L) each for 2 hrs at 50-60° C. The alcoholic extract was fine filtered and concentrated under vacuum to dry powder (100 g).

Example 4

Bio-enrichment of *Aphanamixis polystachya* Extracts

The hydroalcohol extract dry powder (10 g) was extracted thrice with acetone (3×500 mL) at 50° C. each for 1 hour. The combined extracts were concentrated under reduced pressure to give acetone soluble fraction (2 g). The acetone insoluble residue was dried under vacuum to yield 8 g of active fraction as a dry powder. Acetone insoluble fraction (4 g) was subjected to chromatography on reversed phase polymer resin (MCI Gel, CHA20P, 75-150 μL, Mitsubishi Chemical Corporation, Toyko, Japan) and eluted with water, 20% methanol, 40% methanol, 60% methanol and 80% methanol. The fraction eluted with 40% methanol/water was concentrated under reduced pressure to afford a fraction (1.72 g), which exhibits potent 5-Lipoxygenase inhibition.

Example 5

Bioenrichment of *Aphanamixis polystachya* Extracts

The crude hydroalcoholic extract (10 g) was subjected to solvent partitioning between water and ethyl acetate. The organic layer was separated and the aqueous layer was evaporated under reduced pressure to obtain dry powder (9 g). The dry powder (8 g) was dissolved in sufficient water and loaded on to a R20 (Styrene-divinylbenzene Synthetic Adsorbent resin, Mitsubishi Chemical Corporation, Japan) resin column. The column was washed with two bed volumes of water. The compound was then eluted with 60% methanol, and 80% methanol, followed by washing the column with methanol. The fractions eluted with 60%-80% methanol were combined and concentrated to yield the active fraction as a dry powder (4.2 g), which exhibits potent 5-Lipoxygenase inhibition.

Example 6

In-vitro Antioxidant Activity of *Aphanamixis polystachya*
Determination of Superoxide Radical Scavenging Activity:

Superoxide radical scavenging activity of test substances was determined by the method of McCord and Fridovich. The assay mixture contained EDTA (6.6 mM containing 3 μg NaCN), riboflavin (2 μM), NBT (50 μM), various concentrations of test substances and phosphate buffer (67 mM, pH 7.8) in a final volume of 3 mL. The tubes were mixed well and optical densities were measured at 560 nm. The tubes were uniformly illuminated with an incandescent lamp for 15 min. and the optical densities were measured again at 560 nm. The percentage inhibition of superoxide radical generation was measured by comparing the absorbance values of control and those of the test substances. The $IC_{50}$ values were obtained from the plot drawn of the concentration (μg) verses percentage inhibition. The data are summarized in table 1.

TABLE 1

Antioxidant activity of *Aphanamixis polystachya*

| S. No | Test substance | NBT method $IC_{50}$ μg/mL | DPPH method $IC_{50}$ μg/mL |
|---|---|---|---|
| 1 | Aphanamixis_polystachya, MeOH extract | 12 | 5.3 |
| 2 | Aphanamixis_polystachya, hydroalcohol extract | 10 | 5.3 |
| 3 | Aphanamixis_polystachya, water extract | 10.3 | 6.5 |
| 4 | Acetone insoluble fraction of hydroalcohol extract | 17.7 | 6.09 |
| 5 | Bioenriched fraction of MCI column for the hydroalcohol extract | 12.6 | 4.4 |
| 6 | Bioenriched fraction of R20 resin column for the hydroalcohol extract | 10 | 4.0 |
| 7 | Vitamin C | 150 | 4.1 |

Determination of DPPH (1,1-diphenylpicrylhydrazyl) free radical scavenging activity:
DPPH free radical scavenging activity was measured by the method of Lamaison, et al., based on the reduction of coloured methanolic solution of the DPPH. Free radical scavenging ability of each test substances added to the methanolic solution of DPPH was inversely proportional to the difference in initial and final absorption of DPPH solution at 517 nm. Antioxidant activity is expressed as the 50% inhibitory concentration ($IC_{50}$). The reaction mixture contained $1 \times 10^{-4}$ mM methanolic solution of DPPH and various concentrations of the test substances. Percentage inhibition was determined by comparing the absorbance values of test and control tubes. $IC_{50}$ values were obtained from the plot drawn of the concentration (μg) verses percentage inhibition.

Example 7

5-Lipoxygenase Inhibitory Activity of *Aphanamixis polystachya* Extracts and Fractions 5-Lipoxygenase enzyme inhibitory activity was measured using the method of Schewe et al., modified by Reddanna et al. The assay mixture contained 80 μM linoleic acid and sufficient amount of potato 5-lipoxygenase in 50 mM phosphate buffer (pH 6.3). The reaction was initiated by the addition of enzyme buffer mix to linoleic acid and the enzyme activity was monitored as the increase in absorbance at 234 nm. The reaction was monitored for 120 sec and the inhibitory potential of the test substances was measured by incubating various concentrations of test substances two minutes before the addition of linoleic acid. All assays were performed three times. Percentage inhibition was calculated by comparing slope of test substances with that of enzyme activity. The results were shown in table 2.

TABLE 2

5-Lipoxygenase inhibitory activity

| S. No | Test substance | $IC_{50}$ values mg/mL |
|---|---|---|
| 1 | Aphanamixis_polystachya, MeOH extract | 4.0 |
| 2 | Aphanamixis_polystachya, hydroalcohol extract | 3.8 |
| 3 | Acetone insoluble fraction of hydroalcohol extract | 1.08 |
| 4 | Water insoluble fraction. of hydroalcohol extract | 1.30 |
| 5 | Bioenriched fraction of MCI column for the hydroalcohol extract | 1.08 |
| 6 | Bioenriched fraction of R20 resin column for the hydroalcohol extract | 0.80 |
| 7 | 3-O-Acetyl-11-keto-β-boswellic acid | 40 |

Example 8

Tyrosinase Inhibitory Activity of *Aphanamixis polystachya* Extracts and Fractions The *A. polystachya* derived anti-inflammatory extracts were tested for Tyrosinase inhibition. Tyrosinase enzyme inhibitory activity was monitored by analyzing the enzyme substrate interaction between tyrosinase and its substrate L-DOPA. L-DOPA will be converted to dopachrome (475 nm) by the enzyme tyrosinase. Hence the activity can be monitored using kinetic mode of a spectrophotometer. The assay mixture contained 2.5 ml crude tyrosinase enzyme in citrate buffer (pH 4.3). The reaction was initiated by the addition of L-DOPA solution (8 mM) and enzyme activity was monitored as the increase in absorbance at 475 nm. The reaction was monitored for 120 sec and the inhibitory potential of the test substances was measured by incubating various concentrations of test substances with the enzyme, two minutes prior to the addition of substrate (L-DOPA). All assays were performed thrice. Percentage inhibition was calculated by comparing slope of test substances with that of enzyme activity. The results were shown in table 3.

TABLE 3

Tyrosinase inhibitory activity of Aphanamixis polystachya

| S. No | Test substance (Enriched fractions of A. polystachya) | $IC_{50}$ µg/mL |
|---|---|---|
| 1 | Acetone insoluble fraction of hydroalcohol extract | 95.6 |
| 2 | Water insoluble fraction. of hydroalcohol extract | 94.9 |
| 3 | Bioenriched fraction of MCI column for the hydroalcohol extract | 95.0 |
| 4 | Bioenriched fraction of R20 resin column for the hydroalcohol extract | 58 |

Example 9

In vivo Study of Inflammatory Biomarkers and Anti-oxidant Properties of Aphanamixis polystachya The anti-oxidant and anti-inflammatory efficacies of Aphanamixis polystachya extract or fractions were evaluated by an in vivo study in Freund complete adjuvant induced arthritis model of Sprague Dawley rats. The rats of either sex were randomly selected and divided into three groups containing four animals in each group. Rats were supplemented with 50 mg/kg body weight of A. polystachya extract, or prednisolone (10 mg/kg body weight) for 14 days. The animals of control group received only the same volume of 1% Na CMC. At the 14 th day, Freund complete adjuvant (FCA) was injected subcutaneously in the sub-plantar region of the left hind paw of each animal. At the end of experiment, the animals were sacrificed and liver tissue samples were excised and stored in aliquot at −80° C. Blood samples were collected from each animal at a regular interval and paw volumes were measured by Plethysmography equipment after 13 days of FCA inoculation. The difference in volume of edema at the day of FCA injection and at $13^{th}$ day after induction is considered as the inflammatory response. The in vivo anti-inflammatory response of A. polystachya was estimated by calculating, the percentage of inhibition of paw edema when compared with the CMC supplemented control rats and was compared with that of the positive control group supplemented with prednisolone as shown in FIG. 1.

To study the cellular target molecules involved in the inflammatory and oxidative stress pathways, the serum pro-inflammatory bio-markers such as nitrite, tumor necrosis factor-alpha (TNF-α), interleukin-1β (IL-1β) and the levels of lipid peroxidation and glutathoine in the liver samples were measured. The quantitative evaluation of the biomarkers was carried out on ELISA Reader (BioRad, USA) by using ultra-sensitive techniques standardized in our in-house facility.

Results:

Potent pro-inflammatory biomarkers in serum, such as nitrite, TNF-α, IL-1β are reduced by 31.6%, 20.6% and 21%, respectively in the Aphanamixis polystachya supplemented animals when compared with the vehicle supplemented group. Additionally, A. polystachya treated group showed 23.4% and 19.3% inhibitions in liver malondialdehyde (a marker compound for lipid peroxidation) and glutathione, when compared with the control group. The data is summarized in FIG. 2. Moreover, the A. polystachya treated group achieved 34.1% inhibition in paw edema as compared with 47.4% inhibition in prednisolone treated group as shown in FIG. 1. Therefore, these data together explain a potential inhibition of inflammation and oxidative stress in Sprague Dawley rats and are compared with prednisolone, a standard anti-inflammatory drug.

Figure 1:
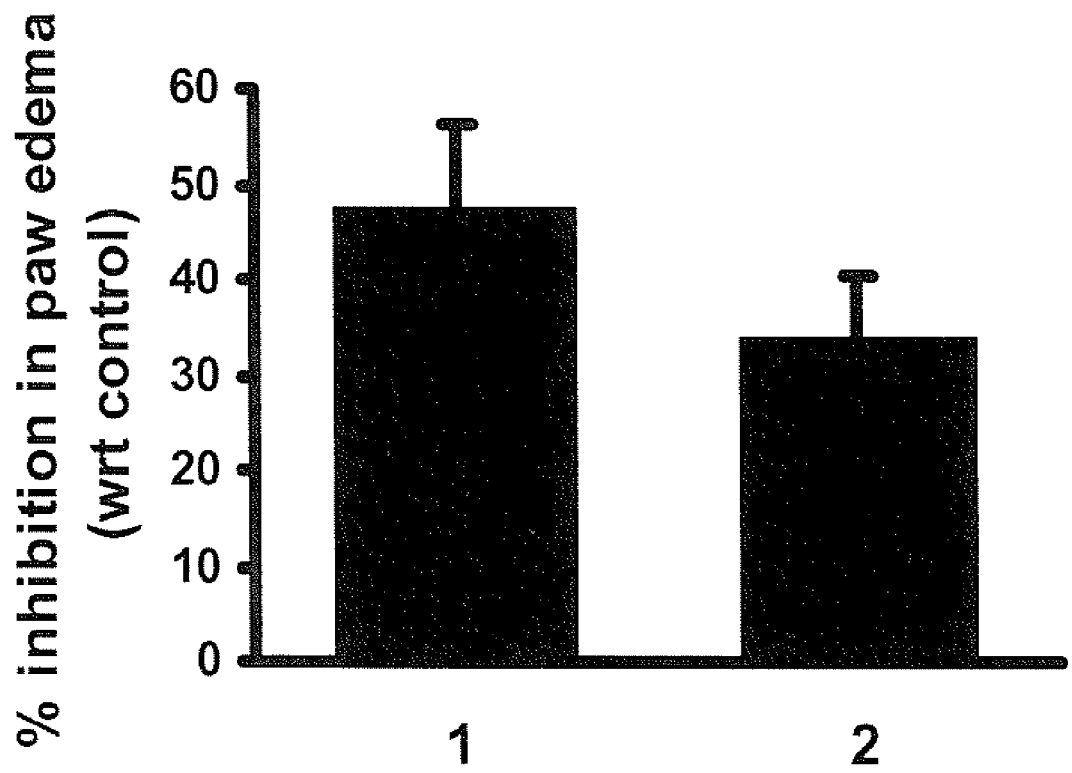
FIG. 1 shows bar diagrammatic representations of inhibition of paw edema volume in Freund's complete adjuvant induced Sprague Dawley rats by Aphanamixis polystachya extract and Prednisolone. The bars 1 and 2 represent groups of rats supplemented with prednisolone (10 mg/kg body weight), and A. polystachya extract (50 mg/kg body weight), respectively.
Figure 2:
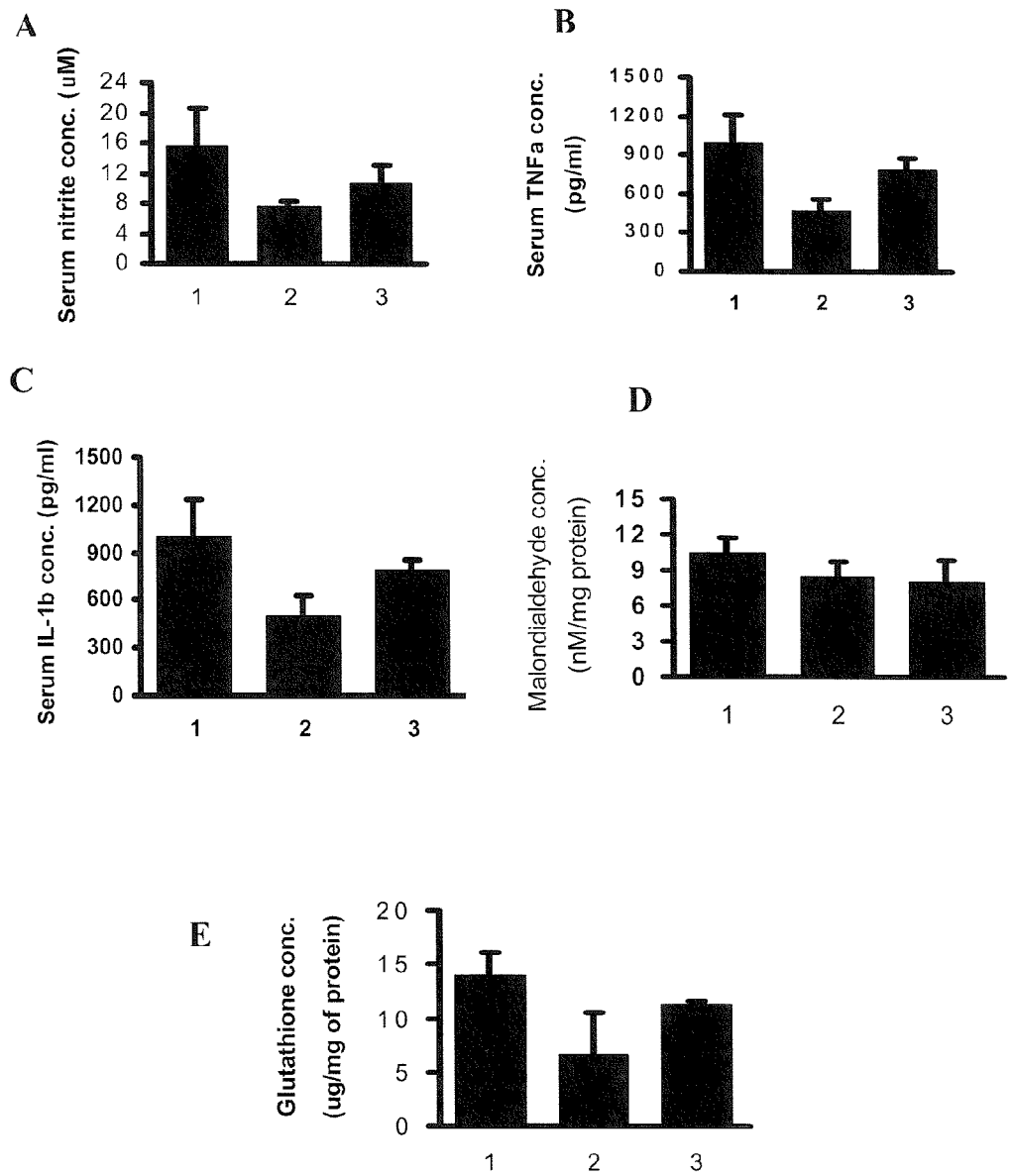
FIG. 2 shows bar diagrammatic representation of inhibitions of pro-inflammatory bio-markers, serum nitrite (A), TNF-α (B) and IL-1b (C), and oxidative stress markers liver malondialdehyde (D) and glutathione (E) by Aphanamixis polystachya extract in Freund's complete adjuvant-induced arthritis in Sprague Dawley rats. Bars 1, 2, and 3, represent 1% CMC supplemented control group, prednisolone group (10 mg/kg body weight), and A. polystachya extract (50 mg/kg body weight) supplemented group respectively.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A method for inhibiting 5-lipoxygenase in an individual in need thereof, comprising
   administering a 5-lipoxygenase inhibitory product containing a therapeutically effective amount of a bioenriched extract of Aphanamixis polystachya bark to said individual,
   wherein said bioenriched extract is prepared by fractionating a hydroalcohol extract of Aphanamixis polystachya by extracting said hydroalcohol extract with acetone to produce:
   an acetone soluble fraction, and
   an acetone insoluble residue;
   wherein said acetone insoluble residue is said bioenriched extract.

2. The method as claimed in claim 1, wherein the individual is a mammal selected from the group consisting of a human, a domestic mammal, and a mammalian farm animal.

3. The method as claimed in claim 1, wherein the 5-lipoxygenase mediated response is associated with a condition selected from the group consisting of autoimmune diseases, arthritic diseases, dermatitis, psoriasis, asthma and allergic diseases.

4. The method according to claim 1, wherein
wherein said 5-lipoxygenase inhibitory product further comprises at least one additional anti-inflammatory agent selected from the group consisting of 3-O-acetyl-11-keto-β-boswellic acid enriched *Boswellia serrata* extracts, enriched curcumin mixtures, enriched demethylated curcumin mixtures, glucosamine, resveratrol, garlic extracts, ginger extracts, chondroitin, methylsulfonylmethane, bromelain, serratio peptidase and quercitine.

5. The method of claim 1, wherein:
said extract of *Aphanamixis polystachya* bark is administered in an amount which is effective to inhibit said 5-lipoxygenase.

6. The method of claim 1, wherein:
said extract of *Aphanarnixis polystachya* bark is administered in an amount which is effective to mediate expression of TNF-α.

* * * * *